US00PP10342P

United States Patent [19]

Sorensen

[11] Patent Number: Plant 10,342

[45] Date of Patent: Apr. 21, 1998

[54] OSTEOSPERMUM PLANT NAMED 'CAPE DAISY CONGO'

[75] Inventor: Carl Aksel Kragh Sorensen, Åbyhoj, Denmark

[73] Assignee: Paul Ecke Ranch, Encinitas, Calif.

[21] Appl. No.: 700,657

[22] Filed: Aug. 9, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV-ROM Plant Variety Database 'Cape Daisy Congo', PBR OST 00008, 1993.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Cape Daisy Congo', particularly characterized by its upright growth habit with excellent light purple flower color, mid-season flowering and medium green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Cape Daisy Congo', and was developed by the inventor Carl Aksel Kragh Sorensen in Aarhus, Denmark in 1992 by crossing *Dimorphotheca chrysanthemifolia* and 'Cape Daisy White Fantasy', an unpatented cultivar.

Asexual reproduction by terminal (stem tip) cuttings taken by me or under my supervision at Peterminde Greenhouse in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique light purple flower color.
2. An upright compact growth habit.
3. Mid season flower response.
4. Well suited for 6" pots, nursery containers, and hanging baskets.

'Cape Daisy Congo' is similar to the cultivar 'Sunny Girl', the plant described and illustrated in co-pending U.S. patent application Ser. No. 08/698,337. The growth habit of 'Cape Daisy Congo' is more upright.

DESCRIPTION OF PHOTOGRAPH

The accompanying colored photograph is a top perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. Three rooted cuttings were transplanted into 26 cm (10 inch) hanging baskets on Dec. 11, 1995. Plants were pinched on Jan. 2, 1996, and received plant growth regulator on January 16 and 31. The values, measurements and observations noted below were taken from plants in bloom on Feb. 29, 1996 and continued to flower through April 1996.

On Apr. 9, 1996, I observed a plant in a 26 cm hanging basket 47 cm tall. This basket had three branched plants with an overall height of 54 cm and an overall width of 68 cm. Each plant had 5 strong branches, originating from within 1.5 cm of the soil line, for a total of 15 branches. Each branch was approximately 29 cm long terminating in a flower. At observation, there were 38 flowers open and 104 flower buds in various stages of development. Three secondary shoots subtend the terminal flower from the top 3 nodes on the primary shoot. These secondary shoots were 23 to 30 cm in length and terminated in a flower.

Color references are made to The Royal Horticultural Society Colour Chart (R.H.S.), except where general terms of ordinary dictionary significance are used.

The Plant

Origin: Seedling from cross pollination.

Parentage: Cross between seed parent *Dimorphotheca chrysanthemifolia* (an unnamed cultivar) and pollen parent 'Cape Daisy White Fantasy'.

Classification:

*Botanical.*—Interspecific hybrid *Dimorphoteca chrysanthemifolia×Osteospermum ecklonis.*

*Common name.*—Osteospermum.

*Cultivar name.*—'Cape Daisy Congo'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth retardant application.*—Standard growth retardant application for 'Cape Daisy Lusaka' includes 1–2 applications of daminozide/butanedioic acid mono (2.2 dimethylhydrazide) at a rate of 2,500 ppm. Applications are made as foliar sprays. Growth retarding chemicals generally reduce height of the plant by ⅓.

Plant description:

A. *Form.*—Symmetrical, upright growing perennial shrub, with good branching characteristics after pinching, giving the plant a full appearance.

B. *Habit of growth.*—Vigorous, mounding habit, producing approximately 20 leaves per stem and terminating in flowers. After the initial flower is formed, typically 3 subordinate axillary shoots develop from the nodes of uppermost leaves producing additional flowering shoots. This process is continuous so long as night temperatures remain below 16° C.

C. *Foliage description.*—1. Leaf shape: Obovate with acuminate tip and attenuate leaf base. 2. Leaf blade size: Mature leaves 7.5–9 cm long and 3 cm wide. 3. Petiole length: Approximately 2.5–3 cm in length. 4. Leaf Margin: Slightly sinuate with 3–5 pointed lobes on either side of the leaf blade. 5. Leaf texture: Slightly undulant and twisted at the tip. (i) Upper surface: Slightly pubescent with short, white trichomes evenly distributed throughout the leaf surface. (ii) Under surface: Glaborous. 6. Leaf color: Dark green. (i) Upper surface: Near R.H.S. 147A. (ii) Under surface: Lighter than R.H.S. 147A. 7. Venation: Palmately branched with a predominate light green mid-rib on the upper surface. One prominent mid-vein is slightly raised on the lower surface. 8. Foliage fragrance: Characteristic Osteospermum plant fragrance, particularly notable when foliage is wet.

Inflorescence description: Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

A. *Flowering habits.*—Flowering is determinate with one primary flower at the end of a long, 22–28 cm pedicel on open flowers. Each pedicel had approximately 3–5 leaflets on the proximates end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates. Rooted cuttings will flower in approximately 13 weeks when pinched 2 weeks after potting, then cultivated at 10°–12° C. for 4 weeks and thereafter grown for 7 weeks at a temperature of 18° C., for a total growing time to flower of 15 weeks.

C. *Flower buds.*—Flower buds develop successively on secondary branches, reaching a size of 2 cm long and 1 cm wide prior to opening.

D. *Flowers borne.*—Singularly 12 cm above the plant canopy.

E. *Quantity of flowers.*—Secondary flowers occur progressively around the primary flower so that tight buds to mature flowers are visible at the same time.

F. *Flower head.*—1. Number of florets: 20–22 ray florets and numerous disk florets, making up a flower disk approximately 1.2 cm in diameter. 2. Shape: Narrow linear florets with obtuse to acute tips and acute bases. Ray florets approximately 4 cm long and 0.9 cm wide. 3. Color: Ray florets are light purple; disk florets are violet-blue. (i) Upper surface of ray florets: Near R.H.S. 75A. (ii) Under surface of ray florets: Longitudinal stripes near R.H.S. 84B alternating with stripes near R.H.S. 85A. (iii) Disk florets: Near R.H.S. 96A. 4. Surface: (i) Upper surface of ray florets: Glabrous. (ii) Under surface of ray florets: Glabrous but pubescent near the base. 5. Flower size: Up to 8 cm in diameter. 6. Flower fragrance: None.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2 to 3 mm long and purple. 6. Ovary: Inferior to florets and green in color.

H. *Resistance.*—1. Frost: Withstands light frost. 2. Root, stem, foliage and flower diseases: Highly resistant.

What is claimed is:

1. A new and distinct cultivar of Osteospermum plant named 'Cape Daisy Congo' as illustrated and described.

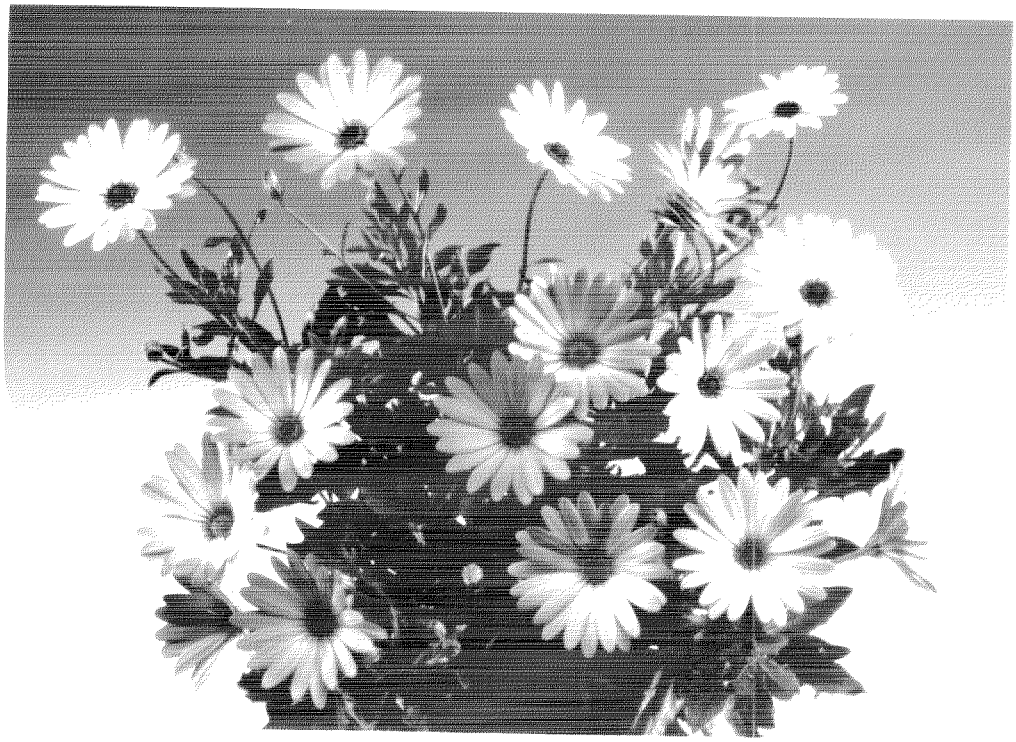

* * * * *